(12) United States Patent
Lapinski et al.

(10) Patent No.: US 9,199,893 B2
(45) Date of Patent: Dec. 1, 2015

(54) PROCESS FOR XYLENES PRODUCTION

(71) Applicant: UOP LLC, Des Plaines, IL (US)

(72) Inventors: Mark P. Lapinski, Aurora, IL (US); Manuela Serban, Glenview, IL (US); Steven L. Krupa, Fox River Grove, IL (US); Mark D. Moser, Elk Grove Village, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 166 days.

(21) Appl. No.: 14/187,522

(22) Filed: Feb. 24, 2014

(65) Prior Publication Data

US 2015/0239804 A1    Aug. 27, 2015

(51) Int. Cl.
| | |
|---|---|
| *C10G 35/085* | (2006.01) |
| *C10G 35/09* | (2006.01) |
| *C07C 2/06* | (2006.01) |
| *C07C 5/05* | (2006.01) |
| *C07C 2/76* | (2006.01) |

(52) U.S. Cl.
CPC .... *C07C 5/05* (2013.01); *C07C 2/76* (2013.01)

(58) Field of Classification Search
CPC ......... C07C 2/06; C10G 35/085; C10G 35/09
USPC .......... 585/322, 319, 510, 517; 208/134, 135, 208/137, 138, 139, 141
See application file for complete search history.

(56) References Cited

U.S. PATENT DOCUMENTS

| | | |
|---|---|---|
| 2,324,165 A | 7/1943 | Layng et al. |
| 2,374,109 A | 4/1945 | Layng et al. |
| 2,380,279 A | 7/1945 | Welty, Jr. |
| 2,604,438 A | 7/1952 | Bannerot |
| 2,689,821 A | 9/1954 | Imhoff et al. |
| 2,697,684 A | 12/1954 | Hemminger et al. |
| 2,767,124 A | 10/1956 | Myers |
| 2,866,745 A | 12/1958 | Heinemann |
| 2,956,005 A | 10/1960 | Lutz et al. |
| 3,767,568 A | 10/1973 | Chen |

(Continued)

FOREIGN PATENT DOCUMENTS

| | | |
|---|---|---|
| EP | 832167 B1 | 4/1999 |
| WO | 2009008879 A1 | 1/2009 |
| WO | 2009067858 A1 | 4/2009 |

OTHER PUBLICATIONS

Adkins, "Effect of Alkali Metal on the Valence State of Re in Reduced Bimetallic Catalysts", Preprints-American Chemical Society, Division of Petroleum Chemistry, Inc., Aug. 1984, pp. 708-713, vol. 29, No. 3.

(Continued)

*Primary Examiner* — Thuan D Dang (57) ABSTRACT

Provided is a process for producing aromatics including the steps of preparing a $C_8$ hydrocarbon stream, feeding a naphtha stream and the $C_8$ hydrocarbon stream to a reforming unit, and reforming the naphtha stream and the $C_8$ hydrocarbon stream to yield aromatics. The process combines a co-feed containing $C_8$ hydrocarbons, an alkali/alkaline earth metal-containing reforming catalyst, and a high temperature operating regime to achieve significant improvements in a reforming process for the production of xylenes and other aromatics.

3 Claims, 6 Drawing Sheets

(56) References Cited

U.S. PATENT DOCUMENTS

| | | |
|---|---|---|
| 3,787,313 A | 1/1974 | Pollitzer |
| 3,992,465 A | 11/1976 | Juguin et al. |
| 4,119,526 A | 10/1978 | Peters et al. |
| 4,172,027 A | 10/1979 | Ham et al. |
| 4,229,602 A | 10/1980 | Brinkmeyer et al. |
| 4,297,150 A | 10/1981 | Foster et al. |
| 4,363,721 A | 12/1982 | Engelhard et al. |
| 4,364,820 A | 12/1982 | DeGraff et al. |
| 4,677,094 A | 6/1987 | Moser et al. |
| 4,732,665 A | 3/1988 | Bennett et al. |
| 4,882,040 A | 11/1989 | Dessau et al. |
| 4,897,177 A | 1/1990 | Nadler |
| 4,966,880 A | 10/1990 | Baird, Jr. et al. |
| 5,198,097 A | 3/1993 | Bogdan et al. |
| 5,242,576 A | 9/1993 | Schmidt et al. |
| 5,417,843 A | 5/1995 | Swart et al. |
| 5,665,223 A * | 9/1997 | Bogdan .................. C10G 35/09 208/138 |
| 5,674,376 A | 10/1997 | Heyse et al. |
| 5,676,821 A | 10/1997 | Heyse et al. |
| 6,048,449 A | 4/2000 | Bogdan et al. |
| 6,809,061 B2 | 10/2004 | Bogdan et al. |
| 7,271,303 B1 | 9/2007 | Sechrist et al. |
| 7,692,052 B2 | 4/2010 | Frey et al. |
| 7,799,729 B2 | 9/2010 | Gajda et al. |
| 8,128,887 B2 | 3/2012 | Bradley et al. |
| 8,470,165 B2 | 6/2013 | Cosyns et al. |
| 8,475,650 B2 | 7/2013 | Wang et al. |
| 2010/0048968 A1 | 2/2010 | Lauritzen et al. |

OTHER PUBLICATIONS

Lu'U, "Kinetics of n-hexane reforming over multimetallic catalysts Pt-Sn-K/Al2O3", Div. Material Sci., Journal of Chemistry-National Centre for Science and Technology of Vietnam, 1996, pp. 39-44, vol. 34, No. 4.

Talyan, "Formability of Stainless Steel", Metallurgical and Materials Transactions, Aug. 1998, pp. 2161-2172, vol. 29A.

Guilemany, "Microstructural Examination of HVOF Chromium Carbide Coatings for High-Temperature Applications", Journal of Thermal Spray Technology, Dec. 1996, pp. 483-489, vol. 5, No. 4.

U.S. Appl. No. 14/187,537, filed Feb. 24, 2014, Moser et al.

* cited by examiner

PROCESS FOR XYLENES PRODUCTION

FIELD OF THE INVENTION

The present invention generally relates to a high temperature reforming process for the production of aromatic hydrocarbons wherein the reforming catalyst comprises an alkali metal, an alkaline earth metal or combinations thereof and the feed is a naphtha/$C_8$ hydrocarbon co-feed.

BACKGROUND OF THE INVENTION

Catalysts having both a hydrogenation-dehydrogenation function and an isomerization/cracking function ("dual-function" catalysts) are used widely in many applications, particularly in the petroleum and petrochemical industry, to accelerate a wide spectrum of hydrocarbon-conversion reactions. The isomerization/cracking function generally relates to a material of the porous, adsorptive, refractory-oxide type containing an acid function. Typically, this material may be utilized as a support or carrier. The hydrogenation-dehydrogenation function is primarily contributed by a metal component (e.g., Group VIII metals) that is combined with the support.

It is of critical importance that a dual-function catalyst exhibit the capability both to initially perform its specified functions efficiently and to perform them satisfactorily for prolonged periods of time. The parameters used in the art to measure how well a particular catalyst performs its intended functions in a particular hydrocarbon reaction environment are activity, selectivity and stability. In a reforming environment, these parameters are defined as follows:

Activity is a measure of the ability of the catalyst to convert hydrocarbon reactants to products at a designated severity level representing a combination of reaction conditions: temperature, pressure, contact time, and hydrogen partial pressure. Selectivity refers to the percentage yield of a desired product from a given feedstock at a particular activity level. Stability refers to the rate of change of activity or selectivity per unit of time or of feedstock processed. Activity stability generally is measured as the rate of change of operating temperature per unit of time/feedstock to achieve a given product, with a lower rate of change corresponding to better activity stability.

One process that often employs a dual-function catalyst is catalytic naphtha reforming. Reforming comprises a variety of reaction sequences, including dehydrogenation of cyclohexanes to aromatics, dehydroisomerization of alkylcyclopentanes to aromatics, dehydrocyclization of an acyclic hydrocarbon to aromatics, hydrocracking of paraffins to light products boiling outside the gasoline range, dealkylation of alkylbenzenes and isomerization of paraffins. Some of the reactions occurring during reforming, such as hydrocracking which produces light paraffin gases, are undesirable as they can have a deleterious effect on the yield of a desired product. Improvements in catalytic reforming technology thus are targeted toward enhancing those reactions effecting a higher yield of a desired product.

In some refineries configured for petrochemical production, it may be desirable to carry out additional processing to maximize the yield of valuable xylenes from the aromatic gasoline produced in the reforming process. The xylene isomers are produced in large volumes from petroleum as feedstocks for a variety of important industrial chemicals. Orthoxylene is used to produce phthalic anhydride, which has high-volume but mature markets. Metaxylene is used in lesser but growing volumes for such products as plasticizers, azo dyes and wood preservers. However, the most important of the xylene isomers is paraxylene, the principal feedstock for polyester which continues to enjoy a high growth rate from a large base demand. In addition, often present in xylene mixtures is ethylbenzene, which is occasionally recovered for styrene production, but usually is considered a less desirable component of $C_8$ aromatics.

The xylenes are not directly recovered from petroleum by the fractionation of naphtha in sufficient volume to meet demand nor in a high enough purity; thus conversion of other hydrocarbons is necessary to increase the purity and yield of the xylenes. For straight run naphtha feedstocks, which may be naphtha distilled out of crude oil, it is necessary to utilize high severity reforming with inter-reactor reheat to convert large amounts of paraffins, such as from about 40 to about 70 weight percent, and having about 30 to about 60% total cyclic content, to the desired xylenes and/or benzene. Moreover, the large amount of non-aromatic content remaining in the reformed naphtha requires substantial subsequent processing to remove the non-aromatics and to transalkylate the aromatics to benzene and xylene.

While the aforementioned dual-function catalysts are capable of catalyzing the dehydrocyclization of paraffins to aromatics such as para-xylene, there is always a trade-off where higher acidity catalysts have more activity but also have reduced selectivity due to increased hydrocracked products, particularly propanes and butanes. Therefore what is needed is a way to eliminate this trade-off where higher selectivity does not come at the cost of lower activity.

SUMMARY OF THE INVENTION

The inventors have made the surprising discovery that significantly more xylene may be produced in a reforming unit by co-feeding a naphtha stream and a $C_8$ olefin stream, for example, from a $C_4$ oligomerization unit. Further improvements in xylene yield may be obtained with reforming catalysts containing alkali metal, an alkaline earth metal or combinations thereof to reduce the acid cracking of the $C_8$ hydrocarbons and to maximize conversion to xylenes. Finally, it has been discovered that operation of the reforming unit in a high temperature regime can improve activity of the aforementioned catalyst while still minimizing cracking reactions. Overall, selecting a co-feed containing $C_8$ hydrocarbons, reforming catalyst comprising an alkali metal, an alkaline earth metal or combinations thereof, and a high temperature operating regime has resulted in significant improvements in a reforming process for the production of xylenes and other aromatics.

One embodiment involves a process for producing aromatics, the process comprising preparing a $C_8$ hydrocarbon stream; feeding a naphtha stream and the $C_8$ hydrocarbon stream to a reforming unit; and reforming the naphtha stream and the $C_8$ hydrocarbon stream to yield aromatics. In an embodiment involving reforming the naphtha stream and the $C_8$ hydrocarbon stream to yield aromatics in the presence of a catalyst, the catalyst may comprise a refractory inorganic oxide support; a platinum group metal; a Group IVA metal; a third metal component selected from the group consisting of an alkali metal, an alkaline earth metal or combination thereof, and a halogen. The catalyst may comprise spherical particles, and the particles may comprise about 0.01 to about 2 wt % of the platinum group metal, about 0.01 to about 5 wt % of the Group IVA metal, about 0.01 to about 1 wt % of the third metal component, and about 0.1 to about 2 wt % of the halogen. The refractory inorganic oxide may comprise alumina. The platinum group metal may be platinum. The Group IVA metal may be tin, germanium, or a mixture thereof. The third metal component may be cesium, rubidium, potassium, sodium, lithium, calcium, strontium, barium, magnesium, and mixtures thereof. In one embodiment, the third metal component is potassium. The particles may comprise about 0.02 to about 0.2 wt % of potassium. The halogen may be chlorine. The reformer may be operated at a temperature greater than 450° C. The reformer may be operated at a temperature greater than 500° C. The reformer may be operated at a temperature greater than 525° C. The reformer may be operated at a temperature greater than 540° C. The reformer may be operated at a temperature greater than 560° C. Preparing the $C_8$ hydrocarbon stream may be by passing $C_3$-$C_5$ hydrocarbon stream to an oligomerization unit. An effluent of the oligomerization unit may be passed to a separation unit; where the effluent of the oligomerization unit may be separated into a first stream and a second stream, the first stream comprising $C_8$ paraffins and $C_8$ olefins; and the first stream may be passed to a hydrotreating unit to yield an at least partially hydrogenated first stream and wherein the $C_8$ hydrocarbon stream may comprise the at least partially hydrogenated first stream.

One embodiment involves a process for producing aromatics, the process comprising: passing $C_3$-$C_5$ hydrocarbon stream to a oligomerization unit; passing an effluent of the oligomerization unit to a separation unit; separating the effluent of the oligomerization unit into a first stream and a second stream, the first stream comprising $C_8$ paraffins and $C_8$ olefins; feeding a naphtha stream and the first stream to a reforming unit; and reforming the naphtha stream and the first stream at a temperature greater than 450° C. to yield aromatics. The process may further comprise hydrotreating at least a portion of first stream prior to feeding to a reforming unit. The catalyst may comprise a refractory inorganic oxide support; a platinum group metal; a Group IVA metal; a third metal component selected from the group consisting of an alkali metal, an alkaline earth metal or combination thereof, and; a halogen.

One embodiment involves a process for producing aromatics, the process comprising: preparing a $C_8$ hydrocarbon stream; feeding a naphtha stream and the $C_8$ hydrocarbon stream to a reforming unit; and reforming the naphtha stream and the $C_8$ hydrocarbon stream at a temperature greater than 450° C. in the presence of a catalyst to yield aromatics; wherein the catalyst comprises a refractory inorganic oxide support; a platinum group metal; a Group IVA metal; a third metal component selected from the group consisting of an alkali metal, an alkaline earth metal or combination thereof, and; a halogen. The catalyst may comprise spherical particles, and the particles comprise about 0.01 to about 2 wt % of the platinum group metal, about 0.01 to about 5 wt % of the Group IVA metal, about 0.01 to about 1 wt % of the third metal component, and about 0.1 to about 2 wt % of the halogen; wherein the refractory inorganic oxide comprises alumina, the platinum group metal is platinum, the Group IVA metal is tin, the third metal component is potassium, and the halogen is chlorine. In other embodiments, the Group IVA metal may be tin, germanium, or a mixture thereof, and the third metal component may be cesium, rubidium, potassium, sodium, lithium, calcium, strontium, barium, magnesium, and mixtures thereof.

These and other features, aspects, and advantages of the present invention will become better understood upon consideration of the following detailed description, drawings and claims.

DETAILED DESCRIPTION OF THE INVENTION

1. Definitions

As used herein, hydrocarbon molecules may be abbreviated $C_1$, $C_2$, $C_3$ ... $C_n$ where "n" represents the number of carbon atoms in the one or more hydrocarbon molecules. $C_n$+ are hydrocarbons with n or more hydrocarbon atoms. $C_n$− are hydrocarbons with n or fewer hydrocarbon atoms.

As used herein, the term "unit" can refer to an area including one or more equipment items and/or one or more sub-units. Equipment items can include one or more reactors or reactor vessels, heaters, exchangers, pipes, pumps, compressors, and controllers. Additionally, an equipment item, such as a reactor, dryer, or vessel, can further include one or more units or sub-units.

As used herein, the terms "alkanes" and "paraffins" may be used interchangeably.

As used herein, the terms "alkenes" and "olefins" may be used interchangeably.

As used herein, the term "weight percent" may be abbreviated as "wt %".

As used herein, the process flow lines in the figures can be referred to interchangeably as, e.g., lines, feeds, mixtures, effluents, portions, parts, products, or streams.

2. Detailed Description

The present invention uses a catalyst comprising (i) a refractory inorganic oxide support, (ii) a platinum group metal, (iii) a Group IVA metal, (iv) a third metal component selected from the group consisting of alkali metals, alkaline earth metals and combinations thereof, and (v) a halogen.

The refractory inorganic oxide support usually is a porous, adsorptive, high-surface area support having a surface area of about 25 to about 500 $m^2/g$. Non-limiting example refractory inorganic oxides include alumina, magnesia, titania, zirconia, chromia, zinc oxide, thoria, boria, silica-alumina, silica-magnesia, chromia-alumina, alumina-boria, and silica-zirconia. Preferably, the inorganic oxide refractory support comprises alumina. Suitable alumina materials are the crystalline aluminas known as the gamma-alumina, eta-alumina, and theta-alumina, with gamma-alumina being preferred. The preferred refractory inorganic oxide will have an apparent bulk density of about 0.3 to about 1.0 g/cc and surface area characteristics such that the average pore diameter is about 20 to 300 angstroms, the pore volume is about 0.1 to about 1 cc/g, and the surface area is about 100 to about 500 m$^2$/g.

The preferred form of the catalyst support is a spherical particle, with a preferred diameter of between about 0.7 and about 3.5 millimeters. Alumina spheres may be continuously manufactured by the well known oil-drop method which comprises: forming an alumina hydrosol preferably by reacting aluminum metal with hydrochloric acid; combining the resulting hydrosol with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and an ammoniacal solution to further improve their physical characteristics. The resulting aged and gelled particles are then washed and dried at a relatively low temperature of about 150° C. to about 205° C. and subjected to a calcination procedure at a temperature of about 450° C. to about 700° C. for a period of about 1 to about 20 hours. This treatment effects conversion of the alumina hydrogel to the corresponding crystalline gamma-alumina.

The platinum group metal comprises platinum, palladium, ruthenium, rhodium, iridium, or osmium, with platinum being preferred. The platinum group metal may exist within the final catalyst as a compound such as an oxide, sulfide, halide, oxyhalide, or as an elemental metal. Best results are obtained when substantially all of the platinum group metal is present in the elemental state. The platinum group metal may be present in the catalyst in any amount which is catalytically effective; the platinum group metal generally will comprise about 0.01 to about 2 wt % of the catalyst, preferably about 0.1 to about 0.4 wt % of the catalyst, and more preferably about 0.2 to about 0.3 wt % of the catalyst.

The platinum group metal may be incorporated in the catalyst in any suitable manner, such as coprecipitation or impregnation. The preferred method of preparing the catalyst involves the utilization of a soluble compound of platinum group metal to impregnate the inorganic oxide support particles in a relatively uniform manner. For example, the platinum group metal may be added to the support by commingling the support with an aqueous solution of chloroplatinic or chloroiridic or chloropalladic acid. Other water-soluble compounds or complexes of platinum-group metals may be employed in impregnating solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium chloride compound, such as chloroplatinic, chloroiridic or chloropalladic acid or rhodium trichloride hydrate, is preferred since it facilitates the incorporation of both the platinum group metal component and a quantity of a halogen in a single step. Hydrogen chloride or the like acid is also generally added to the impregnation solution in order to further facilitate the incorporation of the halogen and the metallic components throughout the inorganic oxide support. In addition, it is generally preferred to impregnate the support material after it has been calcined in order to minimize the risk of washing away the platinum group metal.

The Group IVA metal component in the catalyst may be germanium, tin, or mixtures thereof. In one embodiment the Group IVA metal component is tin. In one embodiment the Group IVA metal component is germanium. The Group IVA metal may be present as an elemental metal, as a chemical compound such as the oxide, sulfide, halide, oxychloride, etc., or as a physical or chemical combination with the inorganic oxide support. Preferably, a substantial portion of the Group IVA metal exists in the finished catalyst in an oxidation state above that of the elemental metal. The Group IVA metal optimally is utilized in an amount sufficient to result in a final catalyst including about 0.01 to about 5 wt % of the Group IVA metal, preferably about 0.1 to about 0.5 wt % of the Group IVA metal, and more preferably about 0.2 to about 0.4 wt % of the Group IVA metal.

The Group IVA metal may be incorporated in the catalyst in any suitable manner, such as by coprecipitation with the inorganic oxide support material, ion-exchange with the inorganic oxide support material or impregnation of the inorganic oxide support material at any stage in the preparation. One method of incorporating the Group IVA metal into the catalyst involves the utilization of a soluble compound of a Group IVA metal to impregnate and disperse the metal throughout the inorganic oxide support material. The Group IVA metal can be impregnated either prior to, simultaneously with, or after the other components are added to the inorganic oxide support material. Thus, the Group IVA metal component may be added to the inorganic oxide support material by commingling the inorganic oxide support with an aqueous solution of a suitable metal salt or soluble compound such as stannous bromide, stannous chloride, stannic chloride, stannic chloride pentahydrate. The utilization of Group IVA metal chloride compounds, such as stannic chloride is particularly preferred since it facilitates the incorporation of both the Group IVA metal and an amount of the halogen component in a single step. When combined with hydrogen chloride during the formation of alumina, a homogeneous dispersion of the Group IVA metal component is obtained in accordance with the present invention.

The catalyst includes a third metal component selected from the group consisting of alkali metal, an alkaline earth metal or combinations thereof. The alkali metals are cesium, rubidium, potassium, sodium, and lithium, and the alkaline earth metals are calcium, strontium, barium, and magnesium. In one embodiment, the third metal component is lithium. In another embodiment, the third metal component is magnesium. In yet another embodiment, the third metal component is potassium. The third metal component optimally is utilized in an amount sufficient to result in a final catalyst including about 0.01 to about 1 wt % of the third metal component. In another embodiment the final catalyst comprises about 0.02 to about 0.5 wt % of the third metal component, and in yet another embodiment the final catalyst comprises about 0.02 to about 0.2 wt % of the third metal component. The alkali metal, an alkaline earth metal a combination thereof can be incorporated into the inorganic oxide support in various ways with impregnation with an aqueous solution of a suitable water-soluble compound being preferred.

An oxidation step can be used in the preparation of the catalyst. The conditions employed to effect the oxidation step are selected to convert substantially all of the metallic components within the catalyst to their corresponding oxide form. The oxidation step typically takes place at a temperature of from about 370° C. to about 650° C. An oxygen atmosphere is employed typically comprising air. Generally, the oxidation step will be carried out for a period of from about 0.5 to about 10 hours.

In addition to the oxidation step, a halogen adjustment step may also be employed in preparing the catalyst. The halogen adjustment step can serve as a means of incorporating the desired level of halogen into the final catalyst. The halogen adjustment step employs a halogen or halogen-containing compound in air or an oxygen atmosphere. Since the preferred halogen for incorporation into the catalyst comprises chlorine, the preferred halogen or halogen-containing compound utilized during the halogen adjustment step is chlorine, HCl or precursor of these compounds. In carrying out the halogen adjustment step, the catalyst is contacted with the halogen or halogen-containing compound in air or an oxygen atmosphere at an elevated temperature of from about 370° C. to about 650° C. Irrespective of the exact halogen adjustment step employed, the halogen content of the final catalyst should be such that there is sufficient halogen to comprise, on an elemental basis, from about 0.1 to about 5 wt % of the catalyst, preferably about 0.3 to about 2.0 wt % of the catalyst, and more preferably about 0.5 to about 1.5 wt % of the catalyst.

In preparing the catalyst, one can employ a reduction step. The reduction step is designed to reduce substantially all of the platinum group metal component to the corresponding elemental metallic state. Preferably, the reducing gas is substantially pure, dry hydrogen (i.e., less than 20 volume ppm water). However, other reducing gases may be employed such as CO, nitrogen, etc. Typically, the reducing gas is contacted with the oxidized catalyst at conditions including a reduction temperature of from about 315° C. to about 650° C. for a period of time of from about 0.5 to 10 or more hours effective to reduce substantially all of the platinum group metal to the elemental metallic state.

The aforementioned catalysts are beneficially used for reforming of hydrocarbon feedstocks to yield aromatic hydrocarbons such as para-xylene. Suitable hydrocarbon feedstocks include naphtha hydrocarbons and more preferably, a blend of naphtha hydrocarbons and $C_8$ hydrocarbons. The $C_8$ hydrocarbons may be obtained in any number of ways. In one embodiment, the $C_8$ hydrocarbon stream is prepared by oligomerizing a $C_3$-$C_5$ hydrocarbon feedstock. In one embodiment the feedstock to the oligomerization system is primarily a C4 hydrocarbon feedstock, for example, from a fluid catalytic cracking (FCC) unit. In one embodiment, any C3 present in the feedstock maybe separated and removed, and the C4 portion of the feedstock oligomerized in a first oligomerization zone. During oligomerization in the first oligomerization zone, any isobutylene readily reacts to form dimers and trimers such as C8 and C12 olefins which are valuable in gasoline and diesel blending, but under proper operating conditions normal butenes may remain substantially unreacted and carried with the oligomerization effluent. The first oligomerization zone effluent is separated into a C4 overhead which contains the unconverted normal butene and a C5+ bottoms product containing the oligomerized hydrocarbon products. The butenes of the C4 overhead stream may be catalytically oligomerized in a second oligomerization zone to form C8 olefins as taught in U.S. Pat. No. 5,169,824 and US 2006/0264686, both of which are hereby incorporated by reference in their entirety, with the product containing up to 20 wt. % trimer. The more linear C8 olefins generated in the second oligomerization zone have poor octane and not as valuable for gasoline blending. The effluent of the second oligomerization zone is used as the C8 hydrocarbon stream that is blended with naphtha hydrocarbons to form the feed to the reforming zone to ultimately produce xylenes, a high value product. In certain embodiments, it may be desirable to further treat the $C_8$ hydrocarbon stream before or after blending with naphtha hydrocarbons to at least partially hydrogenate $C_8$ olefins. In this way, a $C_8$ hydrocarbon stream containing substantially $C_8$ hydrocarbons may be provided to the reforming unit in addition to the naphtha hydrocarbons.

An added advantage of the process described above is the ultimate generation of xylenes, a high value material, from normal butene, a low value material. Further, embodiments of this process may be used to produce xylenes in regions where processes involving methyltertiarybutylether (MTBE) are not available for the removal of isobutylene in the first stage reaction zone, such as, for example, in locations where MTBE cannot be blended into the gasoline pool because of regulatory limitations. Embodiments herein may serve as an alternative to MTBE processes.

Yet another advantage of the process is that the relative amounts of the generation of xylenes and the generation of propylene may be controlled by controlling degree of the normal butene conversion in the first oligomerization zone. The less the normal butene conversion in the first oligomerization zone, the more xylenes that will be generated. Specifically, less conversion of normal butene in the first oligomerization zone results in more unreacted normal butene in the overhead C4 stream, which is fed to the second oligomerization zone resulting in a higher volume of second oligomerization zone effluent that may be co-fed to a reformer for the ultimate generation of xylenes.

On the other hand, the more the normal butene conversion in the first oligomerization zone, the more propylene that may be ultimately generated. Specifically, greater conversion of normal butene in the first oligomerization zone results in a reduced volume of unreacted normal butene in the overhead C4 stream, which is fed to the second oligomerization zone resulting in a lower volume of second oligomerization zone effluent that may be co-fed to a reformer for the ultimate generation of xylenes. The end result is a lower volume of xylenes produced. Instead, the greater conversion of normal butenes in the first oligomerization zone increases the volume of oligomerized products from the first oligomerization zone, a portion of which may be directed, such as a co-feed, to an FCC unit to be cracked and form propylene, a high value product.

The degree of normal butene conversion in the first oligomerization zone is typically controlled by adjusting the operating conditions used in the first oligomerization zone. For example, adjusting the operating temperature results in changes in the degree of normal butene conversion. Adjusting the flow rate of process fluid through the first oligomerization zone also may result in changes in the degree of normal butene conversion. Routing a portion of the process fluid to bypass part of the catalyst in a reactor with multiple catalyst beds is another technique to control the normal butene conversion in the first oligomerization zone. Increasing the amount of recycle to the first oligomerization zone is yet another technique to control the normal butene conversion in the first oligomerization zone.

In regards to use of the catalysts of the present invention in the reforming process, it is desirable to operate the reforming unit within a high temperature regime. A high temperature regime may include temperatures in the range of about 450° C. to about 650° C. More preferably, the temperature range is about 500° C. to about 600° C., and most preferably about 540° C. to about 560° C. The advantage of operating the reforming reactor within a high temperature regime relates to the activity of the catalysts of the present invention comprising an alkali metal, an alkaline earth metal or combination thereof. The addition of, for example, potassium results in increased selectivity for dehydrocyclization but an overall decrease in activity compared to a catalyst without potassium. As a result, increased activity can be obtained by operating the reforming unit at higher temperatures while still maintaining selectivity for conversion to aromatics.

Figure 1:
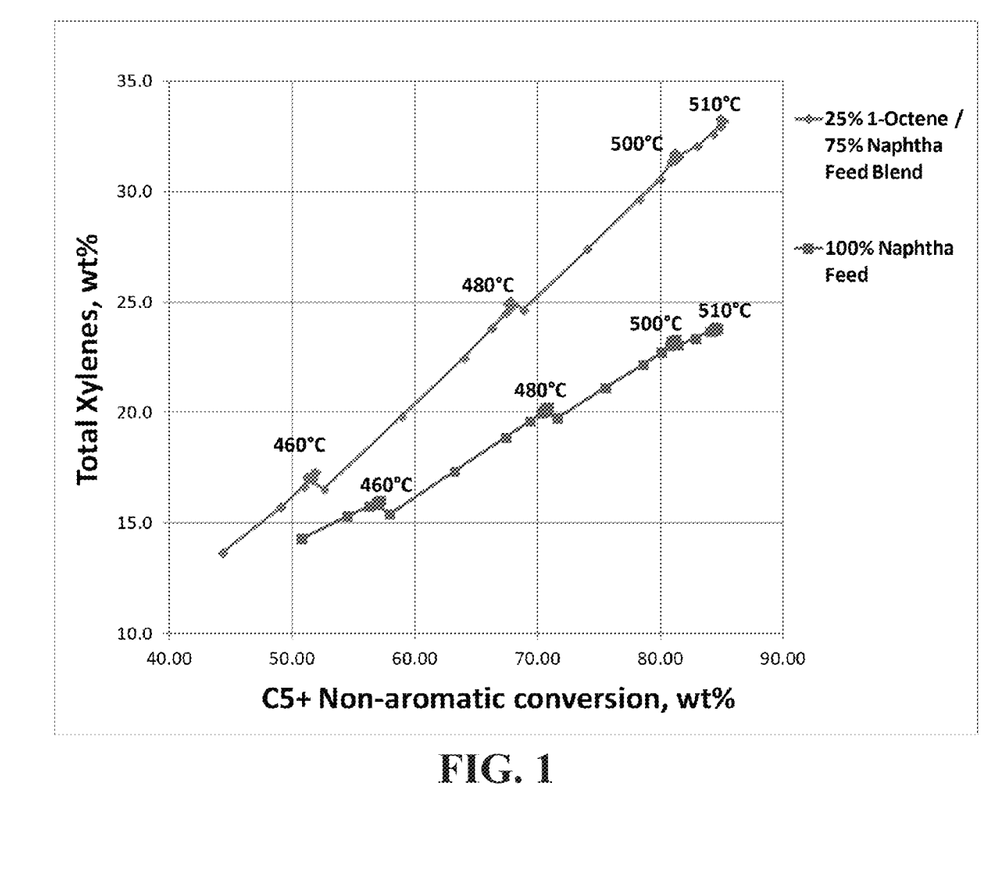
FIG. 1 is a plot of xylene production as a percent of the total effluent stream from a reforming process as a function of $C_5$+ non-aromatic hydrocarbon conversion (wt %) for temperatures between 460-510° C.
Figure 2:
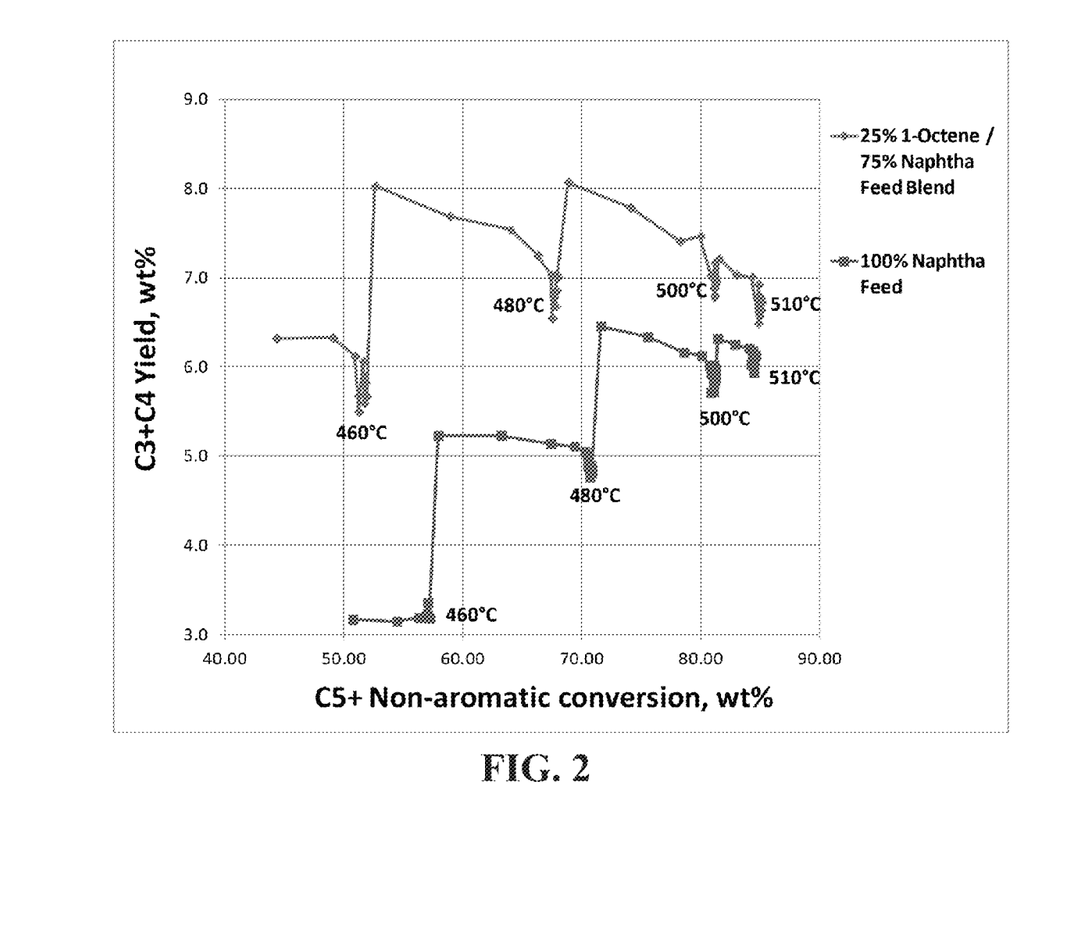
FIG. 2 is a plot of $C_3$ and $C_4$ hydrocarbon production as a percent of the total effluent stream from a reforming process as a function of $C_5$+ non-aromatic hydrocarbon conversion (wt %) for temperatures between 460-510° C.
Figure 3:
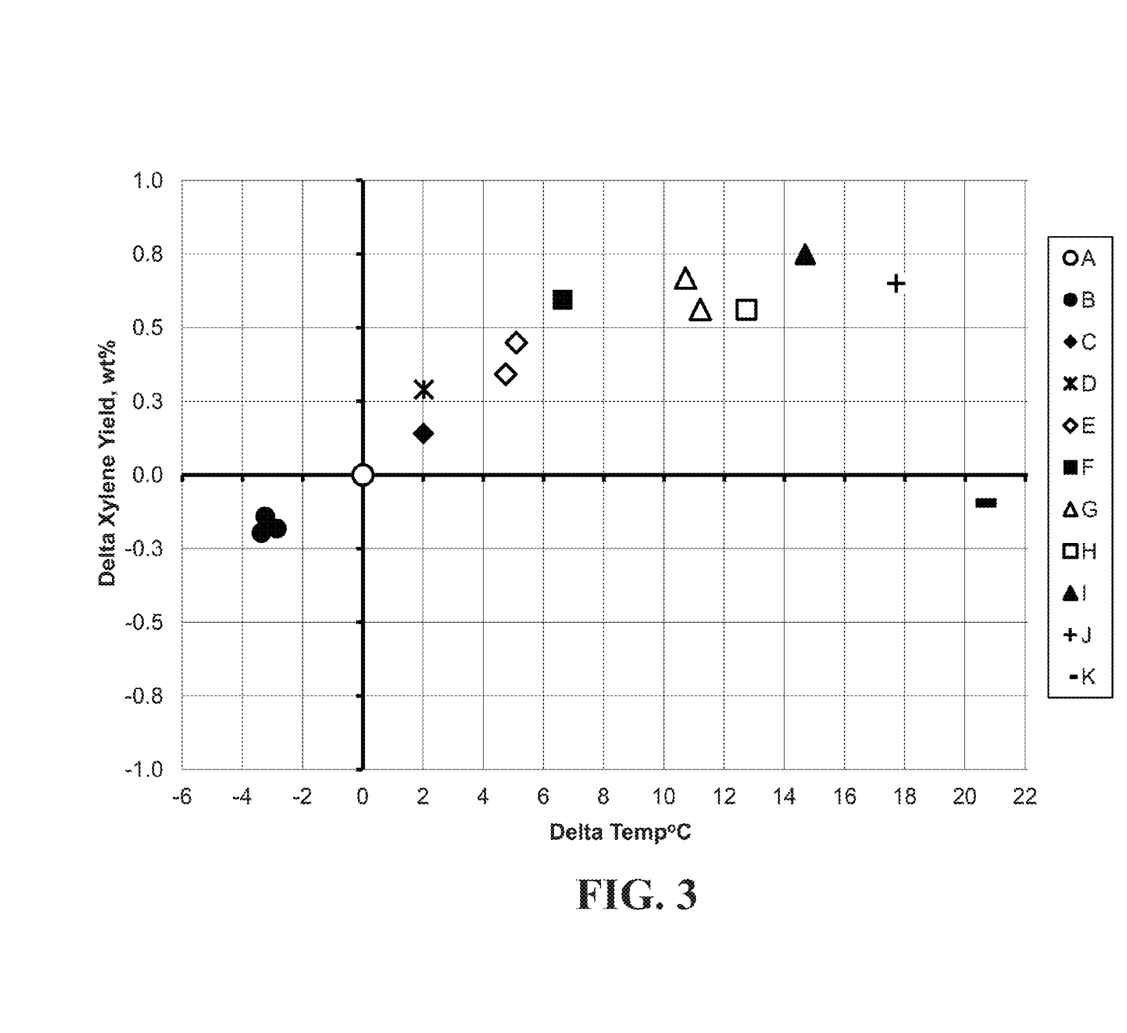
FIG. 3 is a delta plot of para-xylene production as a function of temperature for a series catalysts with varying amounts of potassium. All data is plotted relative to reference catalyst A, which contains 0 wppm K.
Figure 4:
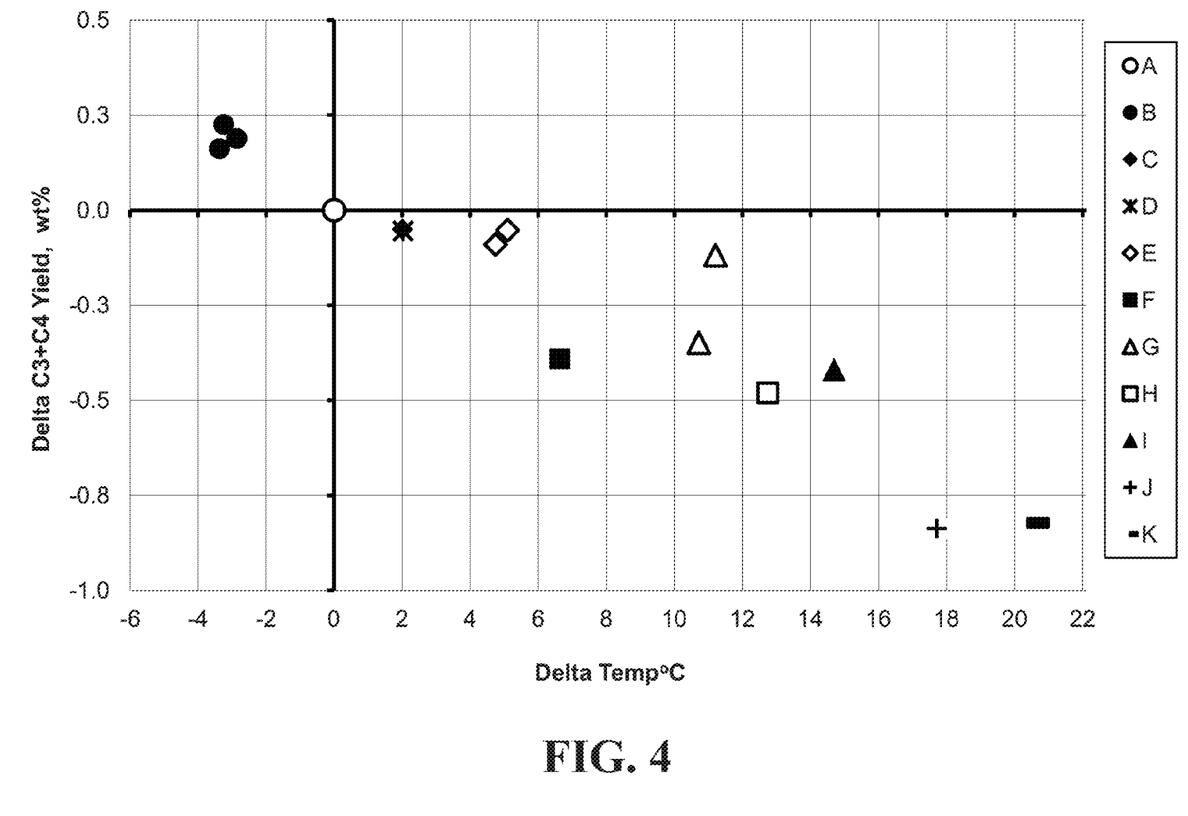
FIG. 4 is a delta plot of $C_3$ and $C_4$ hydrocarbon production as a function of temperature for a series catalysts with varying amounts of potassium. All data is plotted relative to reference catalyst A, which contains 0 wppm K.

Referring now to the Figures, FIGS. 1-2 illustrate the benefit of blending naphtha hydrocarbons with a $C_8$ hydrocarbon stream for reforming to aromatic hydrocarbons. FIGS. 3-4 illustrate the advantages of using an alkali containing reforming catalyst to increase aromatics yield and reduce hydrocracking reactions. FIGS. 1-4 are described in greater detail in the Examples provided herein.

Figure 5:
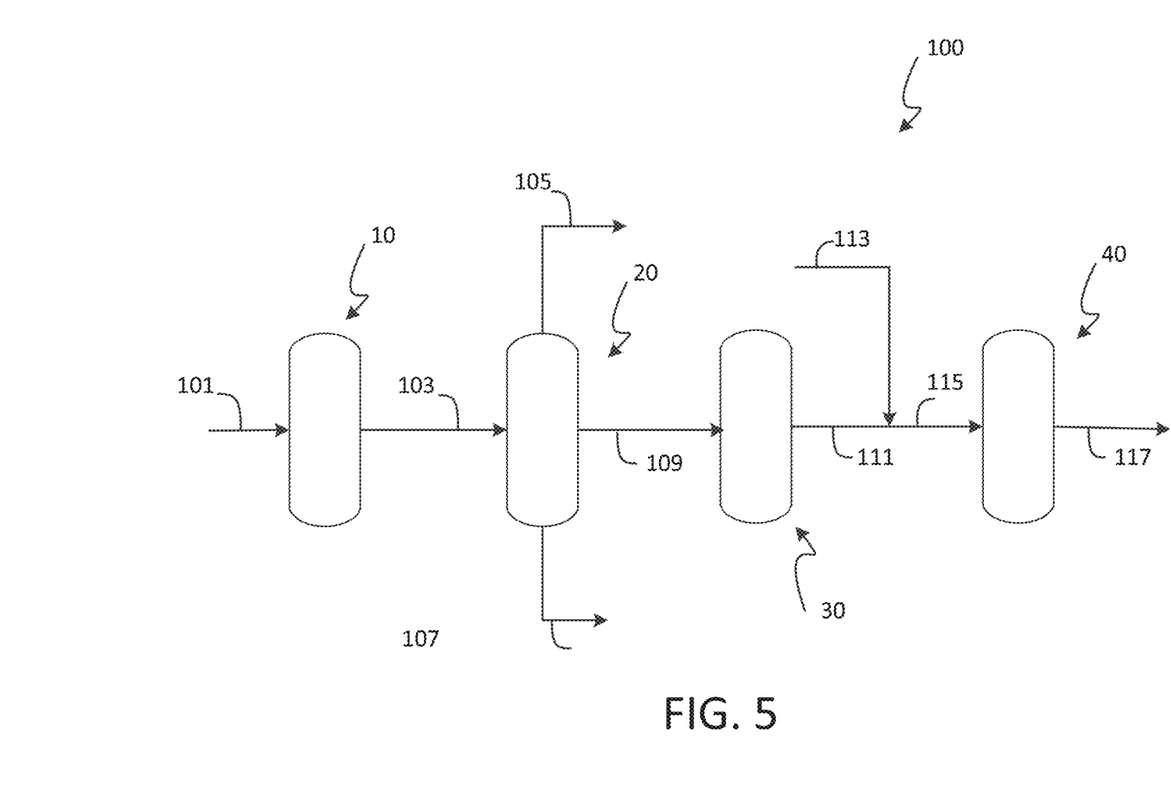
FIG. 5 is an embodiment of a process flow diagram for practicing one embodiment of the invention.

Referring to FIG. 5, an exemplary aromatics production unit 100 includes an oligomerization unit 10, a separation unit 20, a hydrotreating unit 30 and a reforming unit 40. Generally, an oligomerization feed 101 including one or more $C_3$-$C_5$ hydrocarbons can be provided to the oligomerization unit 10. Usually, the oligomerization feed 101 includes both olefins and paraffins. The source of the $C_3$-$C_5$ hydrocarbons can be any process that produces $C_3$-$C_5$ olefinic products such as, but not limited to, cuts of product from a Fluid Catalytic Cracking unit. The $C_3$-$C_5$ stream can be treated prior to its introduction to the oligmerization unit 10 to remove contaminants that would detrimental to the oligomerization process. Typically, the oligomerization unit 10 can be operated at any suitable conditions to form one or more $C_8$+ hydrocarbons, such as oligomerized $C_3$-$C_5$ hydrocarbons, such as $C_8$, $C_9$, $C_{12}$, $C_{16}$ and $C_{20}$ alkenes. One exemplary oligomerization unit 10 can be operated at a temperature of about 30° C. to about 260° C. and a pressure of about 790 kPa to about 8,400 kPa. The oligomerization unit 10 can produce an oligomerization effluent 103. Generally, the oligomerization effluent 103 has an effective amount of one or more alkenes, preferably one or more $C_8$+ alkenes, for producing aromatics, such as paraxylene in the reforming unit 40. The most desired $C_8$ hydrocarbons are linear, single-branched and di-branched. Tri-branched $C_8$ hydrocarbons are more likely to crack to light ends in a catalytic reforming unit instead of isomerizing and reforming to an aromatic. Optionally, effluent 103 can be further processed in an isomerization unit or via other processing steps that reduce the amount of tri-branched $C_8$ hydrocarbons.

The oligomerization effluent 103 can be provided to the separation unit 20. The separation unit 20 can include any suitable separation device, such as a distillation column, operating at any suitable temperature to separate a first stream or stream 105 including one or more $C_7$– hydrocarbons, a second stream 107 including one or more $C_9$+ hydrocarbons, and a third stream 109 comprising $C_8$ hydrocarbons. In one embodiment, second stream 107 comprises substantially C12 olefins wherein substantially may refer to at least 80 mass %, 90 mass % or 95 mass %. In another embodiment, second stream 107 comprises substantially C12 linear olefins wherein substantially may refer to at least 80 mass %, 90 mass % or 95 mass %. In other exemplary embodiments, the separation unit 20 may include other devices in addition or instead of a distillation column, such as a flash drum. In one embodiment, at least a portion of second stream 107 is introduced to hydrotreating unit 30 and or reforming unit 40. The portion of second stream 107 may be combined with naphtha stream 113 before being introduced into reforming unit 40. In another embodiment, at least a portion of second stream 107 is combined with third stream 109 and passed to hydrotreating unit 30 and or reforming unit 40. The portion of second stream 107 may be combined with naphtha stream 113 before being introduced into reforming unit 40.

At least a portion of the third stream 109 containing $C_8$ hydrocarbons, including $C_8$ paraffins and $C_8$ olefins, can be provided to a hydrotreating unit 30. A number of reactions can take place in the hydrotreating unit 30 including hydrogenation of olefins and hydrodesulfurization of mercaptans and other sulfur compounds. In the illustrated embodiment, at least a portion of the $C_8$ olefins are hydrogenated to yield $C_8$ paraffins. Optionally, the naphtha stream 113 may also be provided to the hydrotreating unit 30, or to a second hydrotreating unit (not shown). In another embodiment, a portion of the third stream 109 may be passed around hydrotreating unit 30 (not shown) and may be blended with naphtha stream 113, or may be introduced directly into reforming unit 40.

The at least partially hydrogenated $C_8$ hydrocarbon stream 111 leaving the hydrotreating unit 30 is admixed with a naphtha stream 113 to form a blended naphtha and $C_8$ hydrocarbons stream 115. The blended stream 115 is provided to reforming unit 40, wherein the $C_8$ hydrocarbons and naphtha hydrocarbons undergo dehydrocyclization reactions in the presence of a reforming catalyst to yield aromatic hydrocarbons. The aromatic hydrocarbons preferably include para-xylene and optionally other xylenes such as ortho- and meta-xylene, as well as ethyl benzene. Suitable catalysts include spherical alumina catalysts comprising an alkali metal, an alkaline earth metal or combination thereof such as those described herein. The aromatic hydrocarbons are recovered from the reforming reactor as a product stream 117.

Figure 6:
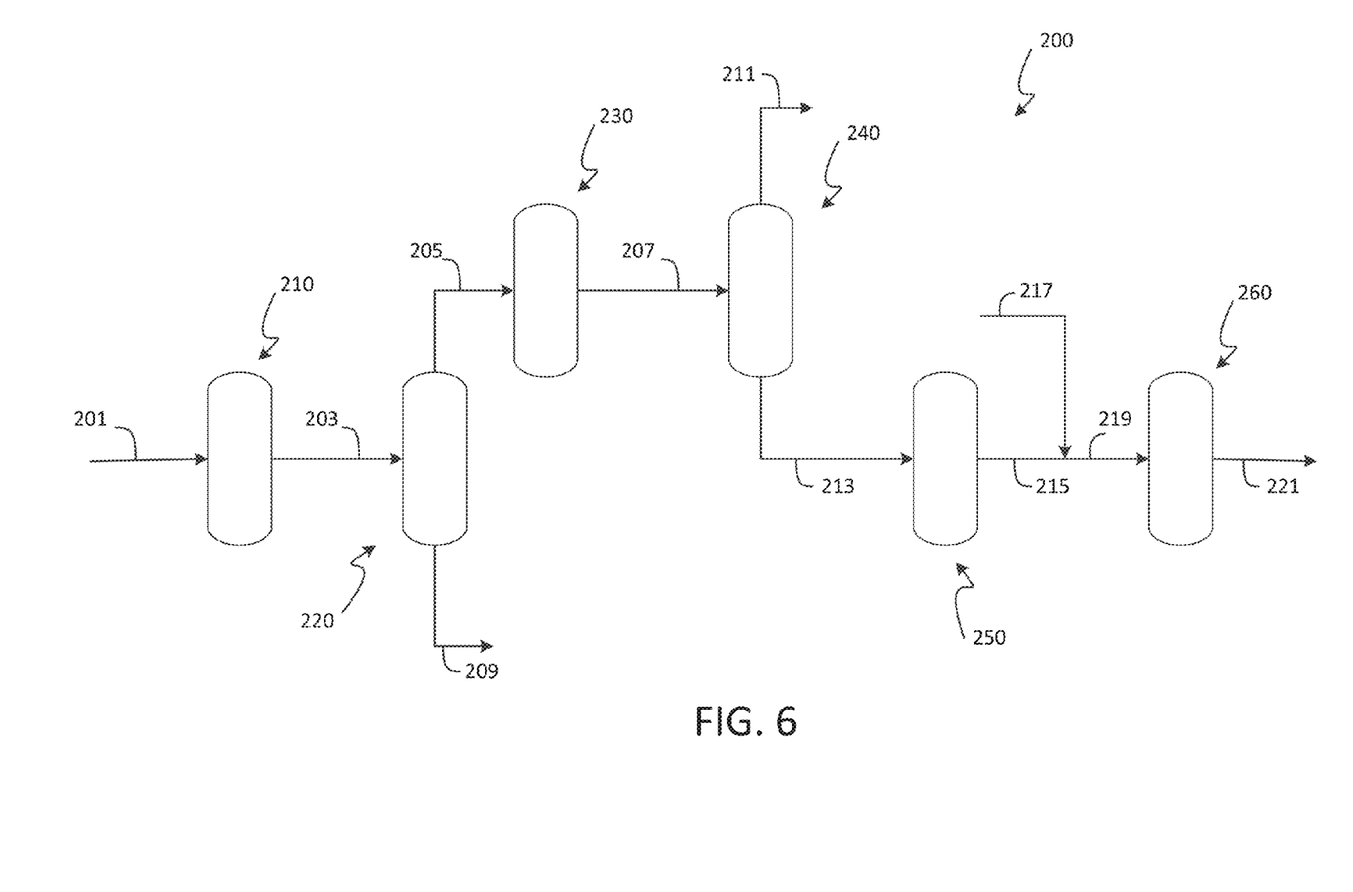
FIG. 6 is an embodiment of a process flow diagram for practicing one embodiment of the invention.

Referring to FIG. 6, an exemplary aromatics production unit 200 includes a first oligomerization unit 210, a first separation unit 220, a second oligomerization unit 230, a second separation unit 240, a hydrotreating unit 250 and a reforming unit 260. Generally, oligomerization feed 201 comprises primarily C4 hydrocarbons, such as butenes, and is provided to the first oligomerization unit 210. A source of oligomerization feed 201 may be one or more cuts of product from a Fluid Catalytic Cracking (FCC) unit. Oligomerization feed 201 can be treated prior to its introduction to the first oligmerization unit 210 to remove contaminants that would detrimental to the oligomerization process, or to remove, and possibly recover, C3 hydrocarbons. Typically, the first oligomerization unit 210 can be operated at any suitable conditions to form one or more oligomerized products such as $C_8$+ hydrocarbons, including for example, hydrocarbons, such as $C_8$, $C_9$, $C_{12}$, $C_{16}$ and $C_{20}$ alkenes. One exemplary oligomerization unit 210 can be operated at a temperature of about 30° C. to about 260° C. and a pressure of about 790 kPa to about 8,400 kPa. The oligomerization unit may contain a first oligomerization catalyst and 210 produces oligomerization effluent 203. Optionally, a hydrogenation unit (not shown) may be in communication with first oligomerization unit 210, for hydrogenation of C8+ oligomers with hydrogenated product recycle. Generally, oligomerization effluent 203 has oligomerized products and unreacted C4 hydrocarbons. It is expected that isobutylene will be nearly completely converted in oligomerization feed 201 and the C4 olefin components of the oligomerization zone effluent 203 will comprise primarily normal butene. Oligomerization zone effluent 203 is introduced into first separation unit 220 where the C4 hydrocarbon portion is separated into first overhead stream 205 and oligomerized products are separated into first bottoms stream 209. First bottoms stream 209 may be further processed to generate gasoline and or diesel blending components.

First overhead stream 205 comprising largely normal butene, is passed to second oligomerization zone 230 such as that described in U.S. Pat. No. 5,169,824 and US 2006/0264686. Second oligomerization zone 230 contains a second oligomerization catalyst that is different from the first oligomerization catalyst. A suitable second oligomerization catalyst is described in U.S. Pat. No. 5,169,824. Second oligomerization unit effluent 207 comprises a mix of C8 olefins, but with a low amount of tri-branched C8 olefins. Since tri-branched C8 hydrocarbons are susceptible to cracking in a catalytic reforming unit, it is desirable to have little to none of the tri-branched C8 hydrocarbons in the second oligomerization zone effluent 207. Second oligomerization zone effluent 207 is introduced to a second separation unit 240. Both first separation unit 220 and second separation unit 240 can include any suitable separation device, such as a distillation column, operating at any suitable temperature to separate the specified overhead and bottoms stream. The second separation unit 240 operates to separate a second overhead stream 211 comprising unreacted C4 hydrocarbons and a second bottom stream 213 comprising the oligomerized products. In other exemplary embodiments, first separation unit 220 and second separation unit 240 may include other devices in addition or instead of a distillation column, such as a flash drum.

Second bottoms stream 213 comprising $C_8$ olefins, may be introduced to an optional hydrotreating unit 250. A number of reactions can take place in the hydrotreating unit 30 including hydrogenation of olefins and hydro desulfurization of mercaptans and other sulfur compounds. Optionally, the naphtha stream 217 may also be provided to the hydrotreating unit 250 (not shown), or to a second hydrotreating unit (not shown). At least partially hydrogenated $C_8$ hydrocarbon stream 215 leaving the optional hydrotreating unit 250 is mixed with naphtha stream 217 to form a blended naphtha and $C_8$ hydrocarbons stream 219. Blended stream 219 is introduced to reforming unit 260, wherein the $C_8$ hydrocarbons and naphtha hydrocarbons undergo dehydrocyclization reactions in the presence of a reforming catalyst to yield aromatic hydrocarbons. The aromatic hydrocarbons preferably include para-xylene and optionally other xylenes such as ortho- and meta-xylene, as well as ethyl benzene. Suitable catalysts include spherical alumina catalysts comprising an alkali metal, an alkaline earth metal or combination thereof such as those described herein. Aromatic hydrocarbons are recovered from reforming reactor 260 as product stream 221.

EXAMPLE 1

A feed blend was made using 25% 1-octene (100% linear $C_8$) and 75% naphtha (61.2 wt % paraffins, 30.6 wt % naphthenes, 8.2 wt % aromatics, 329° F. end point by ASTM D86 distillation). The blend was fed to a reforming pilot plant operating at a liquid hourly space velocity (LHSV) of 1.0 $hr^{-1}$, a molar ratio of hydrogen to hydrocarbon ($H_2$:HC) of 6:1, 50 psi (gauge), with 12 hour temperature holds at 460° C., 480° C., 500° C., and 510° C. A 100% naphtha feed was also run separately over the same catalyst as a comparison case. The catalyst was a high-yield reference catalyst (RC1), which is a lanthanide containing spherical alumina catalyst with 0.30 wt % Sn, 0.29 wt % Pt, 1 wt % Cl and 0 wppm K. FIG. 1 shows that the $C_8$+ naphtha blend produced significantly more xylenes than the naphtha alone. Furthermore, as the conversion increased as a function of increasing temperature, the amount of xylene produced increased for both feeds but there was a larger increase in xylenes for the $C_8$+ naphtha blend, note the steeper slope in FIG. 1.

FIG. 2 shows that the $C_3$+$C_4$ yields from acid-catalyzed cracking were higher for the blend as compared to the Ergon feed alone. The additional paraffin cracking is attributed to the higher overall paraffinic/olefinic content of the blend. However, the differences in C3+C4 yields for the blend vs. the 100% naphtha feed were becoming smaller at higher temperatures indicating that the relative amount of cracking was decreasing as the relative amount of aromatic formation was increasing (FIG. 1). Thus, FIGS. 1 and 2 illustrate the benefit of higher temperature reforming operations for reducing cracking and increasing xylene yields with a $C_8$+ naphtha feed blend.

EXAMPLE 2

A performance evaluation was made using process simulation models to compare the material balance over the reforming unit when naphtha was the reformer feedstock and then when naphtha was mixed with a C8 olefinic stream, the second bottoms stream discussed above, comprising about 18 wt. % normal C8 olefin, 55 wt. % mono-branched C8 olefin, and 25 wt. % di-branched hydrocarbons, with only about 2 wt % tri-branched hydrocarbons. The operating conditions of the reforming unit included a liquid hourly space velocity (LHSV) of 2.30 $hr^{-1}$, a molar ratio of hydrogen to hydrocarbon ($H_2$:HC) of 2.8:1, and 50 psi (gauge). The catalyst in the simulation was a reforming catalyst containing Pt, Sn, and Cl on an alumina support. Table 1 shows that the mixed feed of C8 olefinic feed and naphtha blend produced significantly more xylenes than the naphtha alone, approximately 3 wt % more.

TABLE 1

|  | Naphtha Only feed | Mixed Feed |
| --- | --- | --- |
| Naphtha feed to Reformer, lb/hr | 386,984 | 386,984 |
| C8 Olefinic feed to Reformer lb/hr | 0 | 19172 |
| Total Reformer Feed, lb/hr | 386,984 | 406,156 |
| C8 Aromatics Yield on feed, wt % | 22.4 | 25.5 |
| Hydrogen Yield, wt % | 3.9 | 4.2 |

EXAMPLE 3

A series of spherical alumina catalysts was prepared, which contained 0.30 wt % Sn and a range of K between 0 and 2000 wppm. The catalysts also contained 0.29 wt % Pt and about 1 wt % Cl. 100% naphtha was used to pilot plant test the catalysts at 50 psi (gauge), a liquid hourly space velocity (LHSV) of 1.4 $hr^{-1}$, a molar ratio of hydrogen to hydrocarbon ($H_2$:HC) of 3:1, 8 barrels feed per $ft^3$ catalyst (BPCF) and a research octane number of 104.3 as determined by gas chromatography. The data was adjusted with a kinetic model to a constant 80% conversion of $C_7$ paraffins to show the yield selectivities at a constant conversion level. In addition to RC1, a second reference catalyst (RC2) was tested. RC2 is a lanthanide-free, spherical alumina catalyst with 0.30 wt % Sn, 0.29 wt % Pt, 1 wt % Cl and 0 wppm K.

FIG. 3 demonstrates that K-containing samples produced more xylenes than Catalysts A and B that do not contain K. Catalyst A was a high-yield reference catalyst, which is a lanthanide containing spherical alumina catalyst with 0.30 wt % Sn, 0.29 wt % Pt, 1 wt % Cl and 0 wppm K. Catalyst B was a lanthanide-free, spherical alumina catalyst with 0.30 wt % Sn, 0.29 wt % Pt, 1 wt % Cl and 0 wppm K. All the data was plotted relative to Catalyst A, which corresponds to an absolute yield of 23.5 wt % xylenes from testing a naphtha feed at 513° C. (955° F.) at 1.4 liquid hourly space velocity. The highest xylene yields observed were for Catalyst I with 1100 wppm K operating at a temperature of about 15° C. higher than Catalyst A. The data indicate that at K concentrations over about 1100 wppm K, the xylene yield is decreased. In addition, FIG. 4 shows that $C_3+C_4$ yields that are produced from undesired acid cracking, were observed to decrease with increasing K concentration. Together, FIGS. 3 and 4 show that the combination of K addition and higher temperatures leads to reduced paraffin cracking to $C_3+C_4$ products and increased xylene yields with optimal K concentrations observed for a catalyst containing 1100 wppm K. The catalysts of FIGS. 3 and 4 are described in the Table 2.

TABLE 2

| Catalyst | wppm K | wt. % Cl |
|---|---|---|
| A | 0 | 1.00 |
| B | 0 | 1.00 |
| C | 210 | 1.00 |
| D | 360 | 0.99 |
| E | 400 | 1.02 |
| F | 530 | 1.04 |
| G | 740 | 0.99 |
| H | 900 | 1.05 |
| I | 1100 | 1.02 |
| J | 1400 | 1.04 |
| K | 2000 | 1.02 |

Thus, the invention provides a process for the production of aromatic hydrocarbons wherein the process may use reforming catalyst comprising an alkali metal, an alkaline earth metal or combination thereof, a naphtha/$C_8$ hydrocarbon co-feed, and a high temperature regime.

Those having skill in the art, with the knowledge gained from the present disclosure, will recognize that various changes could be made in the above embodiments without departing from the scope of the present disclosure. Therefore, the scope of the appended claims should not be limited to the description of the embodiments contained herein.

What is claimed is:

1. A process for producing aromatics comprising:
    (a) passing a hydrocarbon stream comprising n-butenes and isobutene to a first oligomerization unit operated under a condition to convert isobutene to form dimers but keep n-butenes unreacted to generate a first oligomerization unit effluent comprising C4 hydrocarbons and at least C8 olefins;
    (b) passing the first oligomerization unit effluent to a separation unit to separate the first oligomerization unit effluent into a first overhead stream comprising C4 hydrocarbons including unreacted n-butenes and a first bottoms stream comprising at least C8 olefins;
    (c) passing the first overhead stream to a second oligomerization unit operated under a condition to convert unreacted n-butene to 1-octene to generate a second oligomerization unit effluent comprising C4 hydrocarbons and 1-octene;
    (d) passing the second oligomerization unit effluent to a second separation unit to separate the second oligomerization unit effluent into a second overhead stream comprising unreacted n-butenes and a second bottoms stream comprising octene-1;
    (e) passing a naphtha stream and the second bottoms stream to a reforming unit containing a catalyst comprising about 0.01 to about 2 wt. % of platinum, about 0.01 to about 5 wt. % of tin, about 0.1 to about 2 wt. of chlorine, about 400 to 1,100 wppm of potassium, and alumina as a support;
    (f) reforming the naphtha stream and the second bottoms stream in the said reforming unit at a temperature greater than 500° C. to yield aromatics including xylenes.

2. The process of claim 1 further comprising hydrotreating at least a portion of second bottoms stream prior to passing to a reforming unit.

3. The process of claim 1 wherein the first oligomerization unit comprises a first catalyst and the second oligomerization unit comprises a second catalyst, wherein the first and second catalysts are different.

* * * * *